United States Patent
Illi

(10) Patent No.: US 6,500,152 B1
(45) Date of Patent: Dec. 31, 2002

(54) DEVICE FOR INTRODUCING FIBRIN ADHESIVE INTO A PUNCTURE CHANNEL

(75) Inventor: Oscar E. Illi, Schwerzenbach (CH)

(73) Assignee: White Spot AG, Baar (CH)

( * ) Notice: Subject to any disclaimer, the term of this patent is extended or adjusted under 35 U.S.C. 154(b) by 0 days.

(21) Appl. No.: 09/720,694

(22) PCT Filed: Jun. 22, 1999

(86) PCT No.: PCT/CH99/00273

§ 371 (c)(1),
(2), (4) Date: Dec. 28, 2000

(87) PCT Pub. No.: WO00/01305

PCT Pub. Date: Jan. 13, 2000

(30) Foreign Application Priority Data

Jul. 2, 1998 (CH) .............................................. 1415/98

(51) Int. Cl.[7] .............................................. A61M 5/178
(52) U.S. Cl. ..................... 604/164.07; 606/213; 604/60
(58) Field of Search ............................... 604/15, 39–43, 604/506, 507, 508, 510, 60, 96.01, 168.01, 171, 523, 529, 533, 286, 285, 164.07; 606/108, 213, 215, 216

(56) References Cited

U.S. PATENT DOCUMENTS 5,676,689 A * 10/1997 Kensey et al. ......... 604/168.01
5,728,132 A     3/1998 Van Tassel et al.

FOREIGN PATENT DOCUMENTS

| EP | 0 482 350 A2 | 4/1992 |
| FR | 2 378 528 | 8/1978 |
| WO | WO 94/28798 | 12/1994 |

* cited by examiner

Primary Examiner—Anhtuan T. Nguyen
Assistant Examiner—Michael M Thompson
(74) Attorney, Agent, or Firm—Pauley Petersen Kinne & Erickson

(57) ABSTRACT

According to the invention a working cannula (1) is fixedly joined to a medical coupling element (3) which is placed onto a sealing cannula (2) and can be screwed onto same. The medical coupling element (3) has an actuating lever (34) and a covering plate (39). When the medical coupling element (3) is rotated by means of the actuating lever (34) in relation to the sealing cannula (2), the working cannula (1) is partially pulled into the sealing cannula (2) to such a depth that inlet openings (11) in the proximal end of the working cannula (1) are drawn into a sealing chamber (14) at the proximal end of the sealing cannula (2). This ensures that the outlet openings (6) through which, for example, fibrin adhesive can be administered into the puncture channel, do not enter an artery. In the insertion position the covering plate (39) simultaneously covers the sealing tube (5) through which the sealing material is injected.

9 Claims, 4 Drawing Sheets

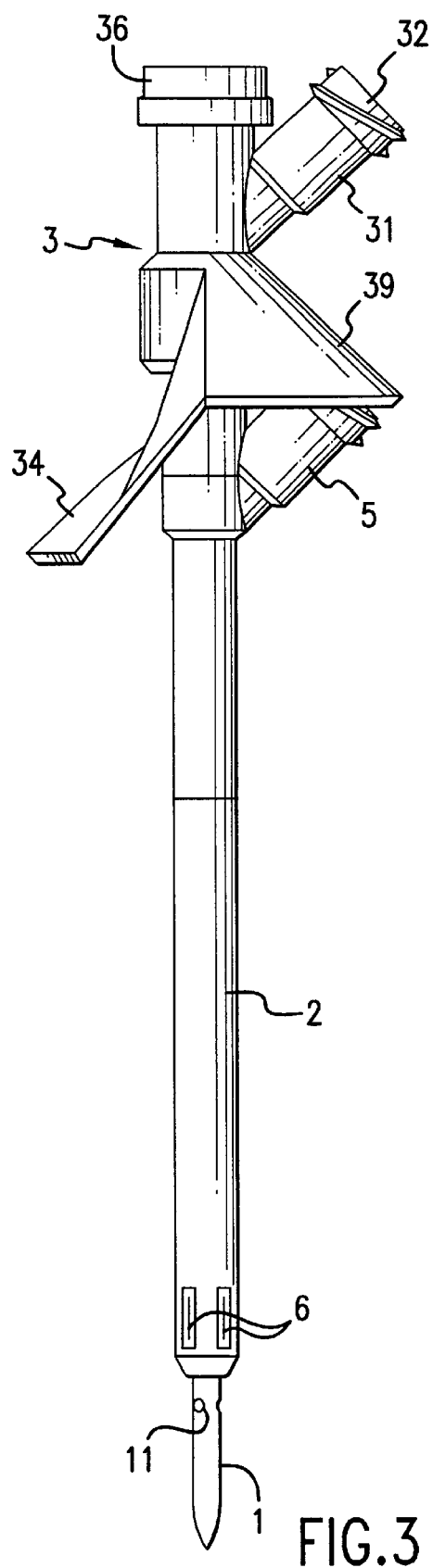
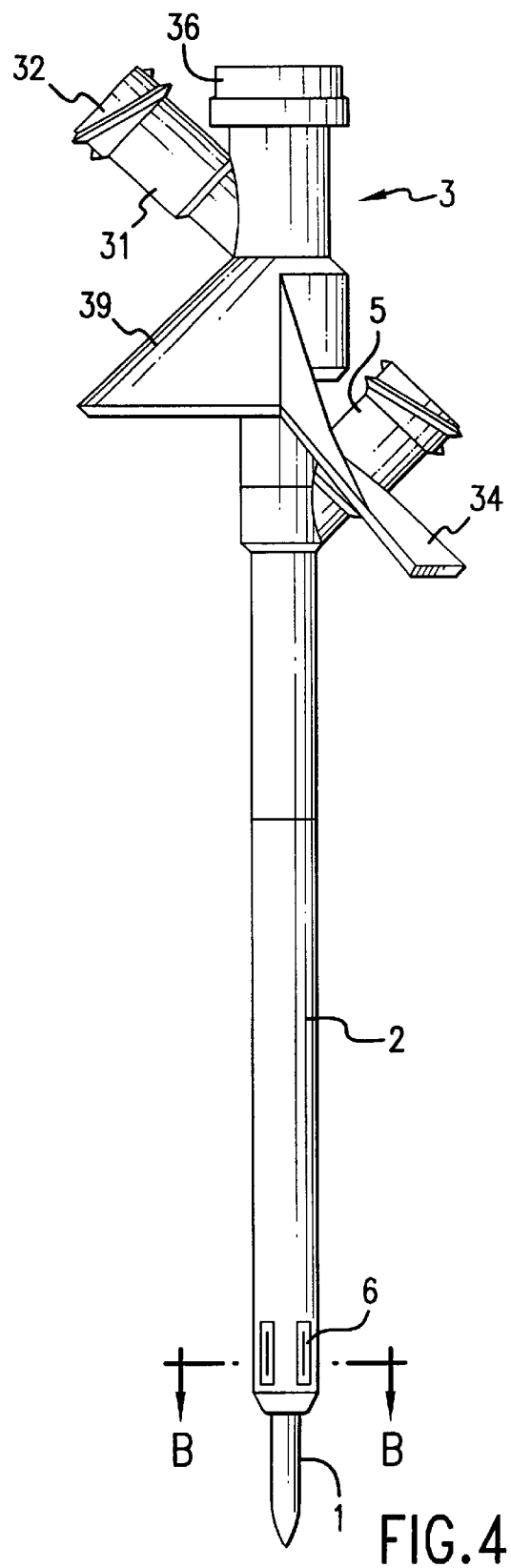
FIG. 3
FIG. 4

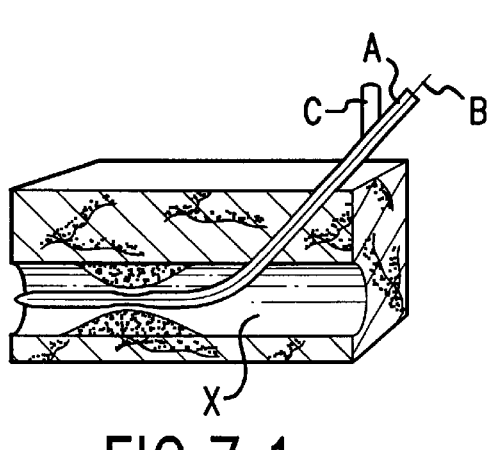
FIG.7.1
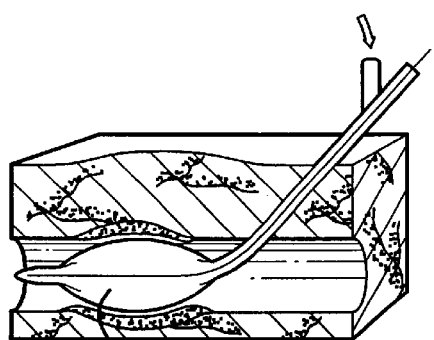
FIG.7.2
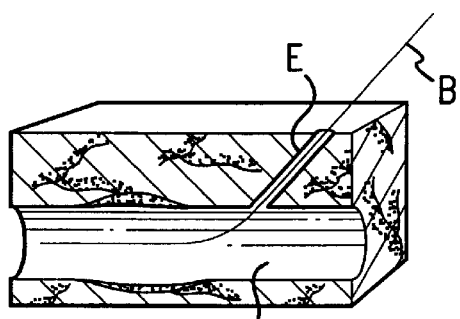
FIG.7.3
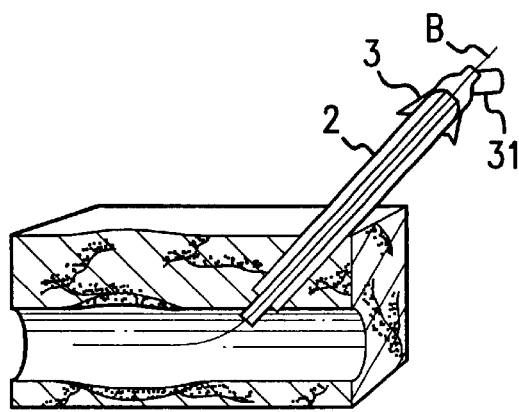
FIG.7.4
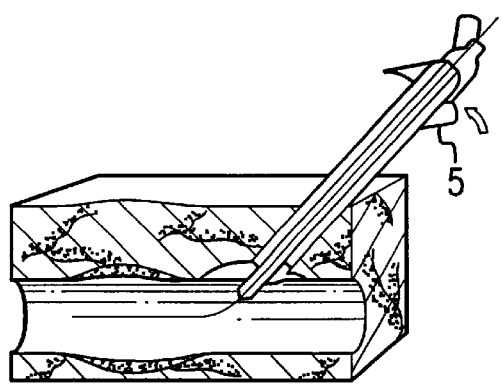
FIG.7.5
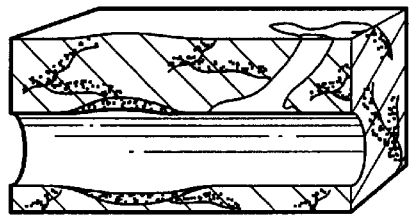
FIG.7.6

DEVICE FOR INTRODUCING FIBRIN ADHESIVE INTO A PUNCTURE CHANNEL

The present invention relates to a device for introducing two-component fibrin adhesive into a puncture channel in the vicinity of an arterial or venal puncture location, according to the preamble of patent claim 1.

Many human and vetinary medical operations demand the puncturing of vessels. In particular with percutaneous transluminar coronary angioplasty (PTCA), heart operations and heart catheterisations the punctured vessels must be closed again with the utmost care. In most cases this is effected by way of direct compression of up to one hour and a pressure compress which must be applied for up to 24 hours and demand 1 to 2 days hospital attendance. As a result there is the desire to find a solution which leads to a quick and secure closure of the puncture location.

On the occasion of a meeting American Heart Association of Nov. 17, 1992 in New Orleans there was presented a method under the description of Vasoseal. With this method in each case two collagen plug of bovine collagen were injected into a puncture channel up to the location of puncture. At the mentioned meeting it was ascertained that apart from the rather seldom rejection reactions of the collagen foreign to the body there arise various further disadvantages or risks. It was ascertained that this system in many cases is ineffective and there exists a certain embolism danger. With about 46% of all cases there formed haemtomas of the magnitude of 2–6 cm. Up to the complete resorption of the bovine collagen there passes weeks to months.

This method leads furthermore to an enlarged scar formation which makes an ultrasound control more difficult. Finally the hospitalisation did not become superfluous but was at least shortened. One of the essential problems however lies in the handling, i.e. the introduction of the collagen plug into the puncture channel. Since after one another two collagen plug must be pressed into the puncture channel, the penetration for example depth for the user is difficult to ascertain. If the collagen plug are injected too deep then the collagen plug may be pushed through the puncture location into the vessel which would lead to a closure or the vessel itself is pressed closed. A new method in order to close such puncture locations quickly, reliably and without the disadvantageous collagen plug has been disclosed by the inventor in WO 94/28798.

From FR-A-2378528 there is known a double-lumen catheter for carrying out a haemodialysis. With this the blood to be dialysised is removed through the exterior lumen and through the interior lumen there is supplied the dialysised blood. The outer lumen at the same time surrounds the inner lumen at a distance and both lumens during the dialysis are introduced into the vessel of the patient.

According to EP-A-0'482'350 there is suggested an apparatus which normally is pushed over the guidewire and with which a plug is inserted into the puncture channel. Although the dilator has a smaller diameter than the cannula into which the guidewire is guided, the resistance which the cardiologist is aware on introduction is so small so that there is an extremely real danger of the outer cannula of the apparatus piercing into the vessel to be sealed. Thus then the plug is placed into the vessel instead of the puncture channel. This danger has been recognised and therefore in the same application it has been suggested, by way of a needle clamp, to measure the penetration depth of the needle when the guidewire is introduced.

It has been shown that with the use of the body's own blood coagulation agents extracted from blood protein in the form of two-component fibrin adhesive whose components at the moment of introduction are mixed and this mixture during or directly after an intravascular operation are introduced into the puncture channel as close as possible to the vessel, there arises an optimal vessel closure. Histological examinations have confirmed these facts.

The solution of sealing the puncture channel with a two-component fibrin adhesive has a high functional safety, as various clinical trials have shown. In spite of the use of blood thinning agents a perfect sealing could not be achieved.

Whilst with the first clinical trials pactically no erroneous handlings were ascertained it has been shown that the high functional safety leads to the fact that with a further series of trials one worked very quickly and the guidelines with respect to precautionary measures were not observed. Accordingly there resulted partly insufficient sealings which required subsequent treatment. Unfortunately the sealing was carried out either too deep, by which means a part of the fibrin adhesive came into the vessel, or the sealing was carried out too far away from the vessel wall, by which means the undelivered fibrin adhesive externally penetrated ushed out on the cannula wall along the puncture channel.

As a consequence it is the object of the present invention to provide a device by way of which fibrin adhesive may be introduced into a puncture channel as exact as possible in the vicinity of an arterial or venal puncture location.

This object is achieved by a device which comprises a sealing cannula which is axially passed through by a working cannula from above to below, wherein the working cannula which serves the intravascular introduction of an instrumentation into a vessel is surrounded by the sealing cannula at a distance so that the fibrin adhesive is led from a connection piece at least from one radially aligned exit opening in the sealing cannula between this cannula and the working cannula, with the features of patent claim 1.

Further advantageous embodiment forms of the device are deduced from the dependent claims, and their significance and advantages are explained in the subsequent description.

In the drawings there is shown a preferred embodiment form of the subject matter of the invention as well as a solution according to the state of the art and these are explained by way of the subsequent description. There are shown in FIG. 1 a device according to the invention in the introduction position and in FIG. 2 in the sealing position, both times in a section, whilst FIG. 3 shows the situation according to FIG. 1 and FIG. 4 the situation according to FIG. 2 in a front view.

Figure 1:
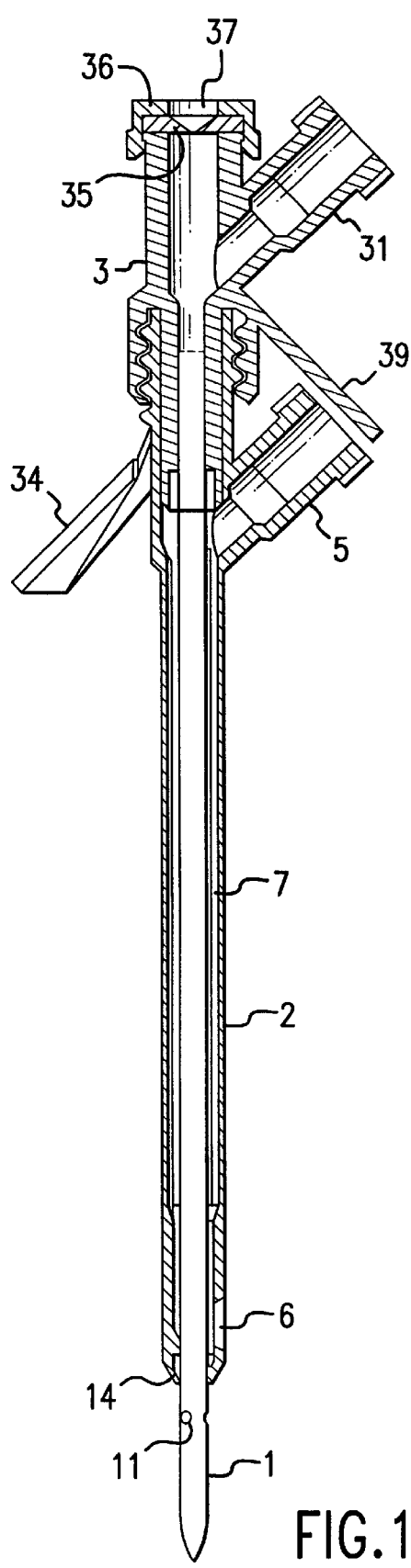

FIGS. 7.1–7.6 show the various steps of the use of the device according to the invention.

The general embodiment form of the device according to the Figures consists only of three parts which may be joined together. With the reference numeral 1 there is indicated the working cannula which in technical language is also called the work sheath. The working cannula itself is only a cylindrical tubelet of plastic which is open at both ends. The front end 1' thereof serves the introduction of the cannula through the puncture location into the opened blood vessel. The working cannula is relatively thin-walled and accordingly comprises a certain bending elasticity. In this embodiment form the working cannula 1 at the other end, the rearward end, is rigidly connected to the medical coupling piece 3. The actual medical coupling piece 3 may for example be a known Luer lock coupling. On the actual medical coupling piece there is formed an exactly machined muff 3' which fits with a positive fit in a sealed manner and in which the working cannula is held. The working cannula 1 runs in the longitudinal direction axially through the sealing cannula 2 and a piece projects downwards far out of the sealing cannula. The sealing cannula 2 is itself also again formed in the shape of a concentric tubelet, but its inner diameter, preferably however also its outer diameter reduces from the top to the bottom, i.e. the inner diameter reduces from the side at which the medical coupling piece 3 is inserted, to the lower end where the working cannula exits the sealing cannula 2.

Over the whole length over which the working cannula 1 is concentrically surrounded by the sealing cannula 2 there thus remains between the working cannula and the sealing cannula a hollow space 7. At the upper end the locking cannula 2 comprises a reinforced sleeve 4 which has a considerably thicker wall thickness than the wall thickness of the sealing cannula 2. In the region of the reinforced sleeve 4 a connection or sealing connect ion piece 5 opens into the sealing cannula 2. By way of this sealing[ c]onnection piece 5 a two-component fibrin adhesive may be introduced into the hollow space 7 between the working cannula and sealing cannula.

The fibrin adhesive may exit from the hollow space 7 only through the exit openings 6 at the lower region of the locking cannula 2. So that fibrin adhesive may not inadvertently penetrate into the blood vessel the exit openings 6 are directed at least approximately radially to the outside. Of course radially is not only to be understood as the direction in the strict geometrical sense. Rather it is to be expressed here that the outflow direction is not axial. Of course the function of the device is already ensured by a single exit opening but one would preferably provide several exit openings 6 distributed on the circumference. Also the configuration of the exit openings 6 as a rule may be designed in any way. For reasons of manufacturing technology one would preferably design these in the form of several longitudinal slots distributed on the circumference.

Although preferably the sealing connection piece 5 is formed on the sealing cannula 2 as one piece directly in the region of the reinforced sleeve, it is of course also possible to manufacture the connection or locking connection piece separately and retrospectively to connect this to the sealing cannula, for example with the help of a thread. Instead of a screw connection of course also a welding or adhesive connection is conceivable. For the mixture of both components of the two-component fibrin adhesive on the market there are already obtainable mixing devices. As a result, for reasons of cost one would dimension the connection piece 5 such that into this one my insert an already obtainable mixing device.

As already mentioned, the wall thickness of the working cannula 1 is very small. It is preferably only a few tenths of a millimeter. Also the hollow space 7 concentric around the working cannula 1 between the outer wall and the inner wall of the sealing cannula 2 is dimensioned extremely small. Since the whole surgical instrumentation must be inserted and ejected through the working cannula 1 it is advantageous to provide means which result in this hollow space 7 being left continually open.

For this on the inner wall of the sealing cannula 2 there are arranged support ribs 9 which preferably run radially.

The support ribs 9 also result in a stiffening of the likewise thin-walled sealing cannula 2. By way of this the danger of a slight contraction of the muscle tissue through which the sealing cannula runs 2 leading to a deformation of the sealing cannula 2 which could close the hollow space 7 is ruled out. In this manner the necessary passage for the fibrin adhesive is secured in all cases.

The essential component of the device according to the invention is the specially formed medical coupling piece 3. This medical coupling piece 3 is rigidly connected to the working cannula 1. Movements which the medical coupling piece 3 carries out are thus transmitted directly to the working cannula 1. The medical coupling piece 3 has a central introduction opening 30 which longitudinally passes through it, is widened at its distal end and at the poximal end blends into a sealing tube piece 38 which sealing fits into the previously described sleeve 4 at the distal end of the sealing cannula 2. The sealing tube piece 38 is surrounded at a distance by a muff 33' formed thereon as one piece, whereby the muff 33' has an inner thread 33. Thanks to this thread 33 the medical coupling piece 3 may be screwed onto the sleeve 4 which at its distal end has an outer thread 20. Obliquely to the central axis, on the medical coupling piece 3 there is formed a control connection piece 31. This connection piece 31 communicates with the introduction opening 30 of the medical coupling piece 31 The control connection piece 31 which is directed upwards, inclined at least approximately at the same angle to the central axis as the previously described connection or sealing connection piece 5 on the sealing cannula 2, has at its end a Luer-lock coupling 32.

The distal end of the introduction opening 30 is closed by way of a leadthrough seal 35. A fixation cap 36 holds the lead-through seal 35 rigidly fixed on the distal end of the medical coupling piece 3. The fixation cap 36 has an introduction hole 37 for leading through the elements to be used intraluminously as for example the guidewire, various catheters, in particular also balloon catheters as well as stents. With the lead-through seal 35 it is particularly the case of a haemostatic seal or a haemostatic valve as is known from various introduction dissecting instruments.

Finally the medical coupling piece 3 as a particularity shows a radially outwardly and downwardly directed cover plate 39 as well as a likewise outwardly directed and downardly inclined actuation lever 34. Also these two parts 39, 34 are formed as one piece with the medical coupling piece 3.

Figure 6:
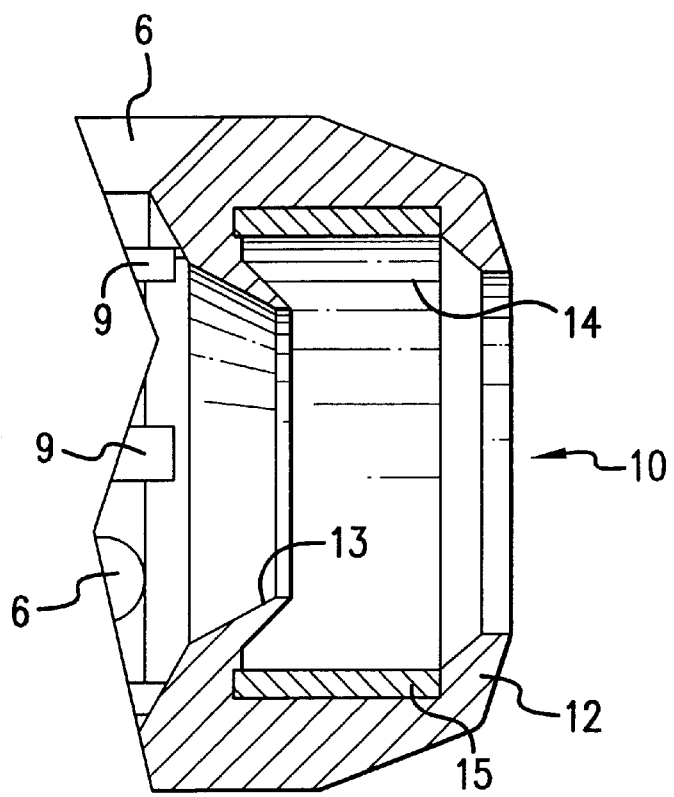
FIG. 6 is again an axial section along the line A—A in FIG. 5.

The purpose of the specially configured medical coupling piece 3 is deduced firstly from the cooperation of this element with the working cannula 1 rigidly arranged thereon and the sealing cannula 2 which is held movable thereto. The sealing cannula 2 not only has the already described exit openings 6 but seen in the proximal direction from these openings a passage opening 10 through which the working cannula 1 with its proximal end is guided in an outwardly and inwardly displaceable manner. Between the actual passage opening 10 and the exit openings 6 the sealing cannula 2 comprises two inwardly directed annular sealing lips 12 and 13. Between the proximal sealing lip 12 and the distal sealing lip 13 there thus remains an annular sealing chamber 14. With respect to this in particular FIG. 6 is referred to. As may be clearly recognised in the FIGS. 1 and 2 as well as 3 and 4 in the proximal end region of the working cannula there is provided at least one but preferably several inlet openings 11. These all lie at one height.

Figure 2:
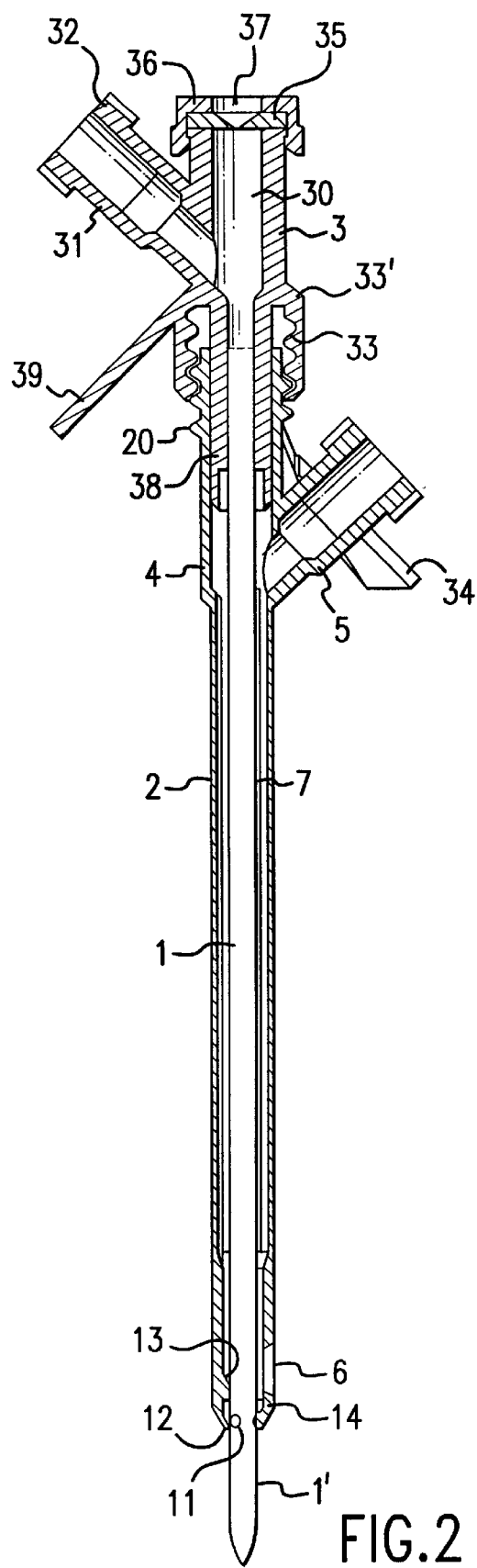
Figure 5:
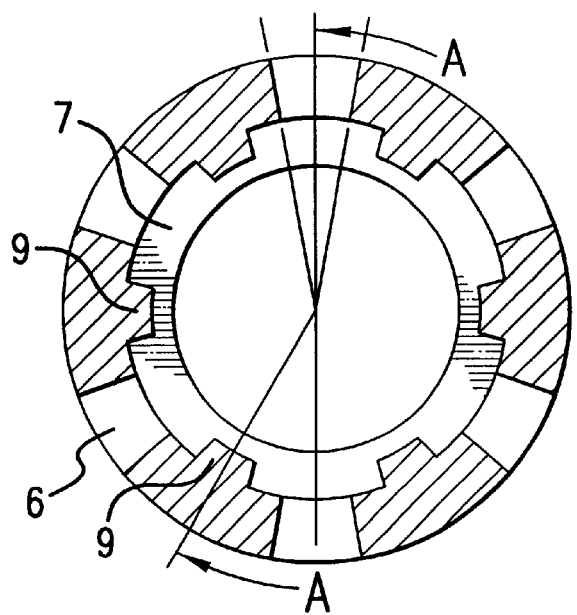
FIG. 5 represents a radial section along the line B—B in FIG. 4.

In the position according to FIGS. 1 and 3 the working cannula is pushed so far to the outside that the inlet openings 11 lie outside the sealing cannula 2, whilst in the FIGS. 2 and 4 they lie within this.

Hereinafter the use of the device according to the invention is explained with reference to the FIGS. 7.1 to 7.6. In FIG. 7.1 one recognises a lumen indicated at X, here a narrowed vessel, for example an artery into which by way of an introduction dissection apparatus A there is introduced a guidewire B. Over this guidewire B in the region of the narrowing there is pushed a balloon catheter D and this is blown up via the connection piece C. From the now correctly widened artery over the guidewire B there is removed the catheter as well as also the introduction dissection apparatus A. Only the guidewire B is left on location. The puncture channel E is now open and the blood flows out through the puncture channel E. Now the device according to the invention is inserted over the guidewire B. The guidewire B at the same time goes through the working cannula 1 as well as the medical coupling piece 3 and penetrates the haemostatic valve 35 and exits through the opening 37 of the fixation lid 36. In this introduction position the device is located in the position as is shown in FIGS. 1 and 3. The working cannula 1 at the same time projects so far out of the sealing cannula 2 that the inlet openings 11 lie free there. During the insertion the elastic tissue of the patient largely closes the inlet openings in the inlet working cannula 1. As a result hardly any blood enters into the working cannula 1. This introduction position is shown in FIG. 7.4. Basically it is not desirable for the physician to prod the sealing cannula 2 into the artery. This may be avoided without any problem by way of the new device. If the physician pushes the device slowly forwards then first the working cannula enters the artery X until the proximal end of the sealing cannula 2 bears on the artery wall. This is indicated to the physician in that now the inlet openings 11 in the working cannula 1 lie in the artery and thus through these inlet openings 11 the blood rises into the working cannula 1 and flows out at the control connection piece 31.

If the physician in spite of this correct position pushes further then before the sealing cannula penetrates into the artery then he will practically first press closed the artery or at least partly so that the pulsating jet of blood is reduced. Thus the physician thus receives a second indication.

As soon as the blood as mentioned flows out of the control connection piece 31 the physician rotates the medical coupling piece 3 by way of the actuation lever 34 about a certain angle of for example 180 degrees. By way of this the medical coupling piece 3 thanks to both the threads 20, 33 is displaced upwards relative to the sealing cannula 2. Corresponding to this the working cannula 1 is drawn into the sealing cannula 2 by this amount. This situation is shown in FIG. 7.5. By way of the rotation of the medical coupling piece 3 to the sealing cannula 2 the cover plate 39 on the medical coupling piece 3 is turned away and thus frees the inlet of the connection and sealing connection piece 5. Now at the sealing connection piece 5 there may be connected a means in order suitably to inject a material for sealing the puncture channel. Thanks to the cover plate 39 it is not possible before the correct placing to connect the sealing material to the sealing connection piece 5.

By way of the mentioned rotation of the medical coupling piece 3 to the sealing cannula 2 the mentioned inlet openings 11 get into the previously described inner region of the sealing cannula 2. This region is the sealing chamber 14 which is suitably dimensioned such that the distance between the proximal sealing lip 12 and the distal sealing lip 13 is larger than the diameter of the inlet openings 11.

Although the previously described means permit an unambiguous positioning of the sealing cannula 2 to the artery directly on the puncture location, often there is in spite of this the desire for the correct positioning also to be visible.

This with the present invention is achieved in that in the sealing chamber 14 between the two sealing lips 12 and 13 one has arranged a ring 15. This ring 15 is dimensioned so small that it is only recognisable in FIG. 6.

The ring 15 basically may be metallic or also yet consist of a coating which is radiologically recognisable. Also conceivable would be a plastic ring which is manufactured of a material to which radiologically recognisable substances have been mixed. In particular various barium mixtures are known to be suitable. In particular metallic rings are suitable for sonographically determining the position of the proximal end of the sealing cannula.

In spite of the high safety on sealing puncture channels which may be achieved with the apparatus according to the invention, this increased safety is achieved with a device which is hardly any more expensive.

What is claimed is:

1. In a device for introducing a two-component fibrin adhesive into a puncture channel into a vicinity of an arterial or venal puncture location, the device having a sealing cannula (2) passed through axially from above to below by a working cannula (1) which provides an intravascular introduction of an instrumentation into a vessel, the working cannula (1) surrounded by the sealing cannula (2) at a distance so that the fibrin adhesive passes from a connection piece (5) to at least one radially directed exit opening (6) in the sealing cannula (2) between the sealing cannula (2) and the working cannula (1), the sealing cannula (2) at a distal end laterally formed as one piece with one of a sleeve and a wall thickening (4), the improvement comprising: the sleeve (4) at a distal region having an outer thread (20) on which a medical coupling piece (3) with an inner thread is threadedly attached, the medical coupling piece (3) having a distal introduction opening (30) and rigidly connected flush to the working cannula (2) which at a proximal end has inlet openings (11) which by a relative movement of the medical coupling piece (3) to the sleeve (4) into a closure position are movable into the sealing cannula (2), wherein on the medical coupling piece (3) there is attached a cover plate (39) in a distanced manner so that the cover plate (39) covers the connection piece (5) when the inlet openings (11) are in an opening position and frees the connection piece (5) when the inlet openings (11) are in the closure position.

2. In the device according to claim 1, wherein the medical coupling piece (3) comprises a lateral control connection piece (31).

3. In the device according to claim 2, wherein on the control connection piece (31) is arranged a Luer-lock coupling (32).

4. In the device according to claim 1, wherein the medical coupling piece (3) has an inner thread (33) which meshes with an outer thread (20) on the connection piece (5) so that by rotating the medical coupling piece (3) with respect to the sleeve (4) the inlet openings (11) are movable into the closure position within the sealing cannula (2) and into the opening position outside of the sealing cannula (2).

5. In the device according to claim 1, wherein on the medical coupling piece (3) is formed an actuation lever (34).

6. In the device according to claim 1, wherein at an end of the medical coupling piece (3) a lead-through seal (35) is held with a fixation (36).

7. In the device according to claim 6, wherein the lead-through seal (35) is a haemostasis valve.

8. In the device according to claim 1, wherein the distal end of the sealing cannula (2) has two radially and inwardly directed annular sealing lips (12, 13) distanced from one another at least by a diameter of the inlet openings (11) and which sealingly bear on the working cannula (1) and which form an annular sealing chamber (14).

9. In the device according to claim 1, wherein in the sealing chamber (14) there is arranged one of a radiologically and sonologically recognizable ring (15).

* * * * *